(12) United States Patent
Howe

(10) Patent No.: US 8,641,938 B2
(45) Date of Patent: Feb. 4, 2014

(54) DENTURE AND METHOD AND APPARATUS OF MAKING SAME

(75) Inventor: Devon O. Howe, Saratoga Springs, NY (US)

(73) Assignee: CMP Industries LLC, Albany, NY (US)

( * ) Notice: Subject to any disclaimer, the term of this patent is extended or adjusted under 35 U.S.C. 154(b) by 0 days.

(21) Appl. No.: 13/571,468

(22) Filed: Aug. 10, 2012

(65) Prior Publication Data

US 2013/0101962 A1    Apr. 25, 2013

Related U.S. Application Data

(60) Provisional application No. 61/539,970, filed on Sep. 27, 2011.

(51) Int. Cl.
*B29C 43/20* (2006.01)

(52) U.S. Cl.
USPC .......................................... 264/16; 433/202.1

(58) Field of Classification Search
USPC ........ 264/16, 17, 19, 20, 138; 433/213, 202.1
See application file for complete search history.

(56) References Cited

U.S. PATENT DOCUMENTS

| | | |
|---|---|---|
| 2,514,076 A | 7/1950 | Kelly |
| 3,126,429 A | 3/1964 | Saffir |
| 4,115,488 A | 9/1978 | Colpitts |
| 4,970,032 A | 11/1990 | Rotsaert |
| 5,151,044 A * | 9/1992 | Rotsaert ..................... 433/229 |
| 5,452,219 A | 9/1995 | Dehoff et al. |
| 5,672,305 A * | 9/1997 | Kogure ..................... 264/102 |
| 5,823,778 A | 10/1998 | Schmitt et al. |
| 6,488,503 B1 * | 12/2002 | Lichkus et al. ............ 433/202.1 |
| 7,431,545 B2 | 10/2008 | Suttor et al. |
| 7,686,989 B2 | 3/2010 | Van Der Zel |
| 7,943,068 B2 | 5/2011 | Panzera |
| 7,981,531 B2 | 7/2011 | Rheinberger et al. |
| 2009/0023112 A1 | 1/2009 | Ganley et al. |
| 2009/0026643 A1 | 1/2009 | Wiest et al. |
| 2009/0287332 A1 | 11/2009 | Adusumilli et al. |

* cited by examiner

*Primary Examiner* — Galen Hauth
(74) *Attorney, Agent, or Firm* — John M. Hammond; Patent Innovations LLC

(57) ABSTRACT

A method for making a denture comprising a base and a plurality of teeth joined thereto. The method comprises forming a first cavity in a block of a denture base material, the first cavity being formed to match the contour of natural teeth as arranged on maxillae or on a mandible; filling the first cavity with a first fluid synthetic tooth material and solidifying the first fluid synthetic tooth material into a first solid synthetic tooth material; removing a portion of the first solid synthetic tooth material to form the plurality of teeth; and removing a portion of the block of denture base material to form the denture base. The steps of the method may be implemented by a computer. An apparatus for making the denture according to certain embodiments of the method, and a denture comprised of a base and artificial teeth are also disclosed.

19 Claims, 7 Drawing Sheets

DENTURE AND METHOD AND APPARATUS OF MAKING SAME

CROSS-REFERENCE TO RELATED PATENT APPLICATIONS

This application claims priority from U.S. Provisional Patent Application No. 61/539,970, filed Sep. 27, 2011, the disclosure of which is incorporated herein by reference.

BACKGROUND

1. Technical Field

Dental prostheses and apparatus and methods of manufacturing them. In particular, computer-implemented methods of manufacturing dental prostheses, a computer-aided system for manufacturing dental prostheses, and dental prostheses made by the system and method.

2. Description of Related Art

Heretofore, the manufacturing of dental prostheses has been a highly labor intensive process requiring multiple fittings to a patient in need of them, and many steps that must be performed at the hands of skilled artisans. The dental prostheses may be a complete upper and/or lower set of prosthetic teeth and their mountings, i.e., dentures, or partial dentures, crowns, bridges, and the like.

By way of illustration, the following are the steps currently practiced in many "dental laboratories" for the fabrication of a conventional fixed dental prosthetic known as a crown:

1) A dentist prepares the tooth (or teeth) to be fitted with a fixed prosthetic by removing tooth structure that is decayed or to allow for space needed by the prosthetic device.
2) An accurate impression of the patient's existing gums and prepared teeth is made by the dentist at the dentist's office.
3) Gypsum material is poured into the impression to form a model (replica) of the dentition to be treated.
4) Wax is typically used to make a coping (thin metal substructure) on the model.
5) Using the "lost wax technique", the wax is invested (covered) by a phosphate investment material and then it is heated to burn-out (remove) the wax, leaving a void in its place.
6) Metal is cast into the void created by the loss of wax to create a metal coping.
7) The metal coping is finished with grinding stones and typically heat-treated.
8) Porcelain powder dispersed in water is painted onto the metal coping.
9) The porcelain is fired in a furnace to sinter it into a continuous hard coating, resulting in the finished crown.

It can be seen that in the above highly labor-intensive process, each of these steps introduces a potential for a processing error. Even the slightest error, such as the investment being too cool, or the powder/water ratio of the investment being incorrect may cause the crown to fit too tightly in the patient's mouth, resulting in improper occlusion (upper and lower teeth engagement). The crown may thus have to be scrapped or reworked through at least one iteration of additional process steps at considerable cost to the patient, dentist, and/or manufacturing lab.

Currently, Computer Aided Design and Computer Aided manufacturing (CAD/CAM) for "fixed" restorative dentistry has evolved to the point where a digital impression can now be made in the dentist's office and the entire process can be computer implemented. However, certain shortcomings still remain in fixed restorative dentistry as presently practiced. For example, subtle irregularities often found in anterior (front) teeth are difficult to replicate using CAD/CAM processes. Manual methods of making anterior fixed prosthetics enable unlimited aesthetic options, only limited by the creativity of the artisan (dental laboratory technician). Some CAD/CAM techniques involve the use of milling a monolithic block of ceramic that does not deliver optimal aesthetics (example: too opaque), especially for anterior applications. For example, most natural teeth exhibit translucency and subtle color variations. A common solution for this problem is for a dental technician to apply a stain and/or glaze of porcelain over the prosthetic made by CAD/CAM. However, this manual step may defeat the primary benefit of CAD/CAM: precise dimensional accuracy.

With regard to the manufacturing of removable dental prosthetics, such as dentures and partials, implementation of CAD/CAM has begun to occur. A key technology that is used in CAD/CAM denture manufacturing is "fused deposition modeling" (FDM). In FDM, a computer-controlled machine builds a three dimensional part by ejecting microscopic droplets of material while repeatedly traversing in an x-y plane, building the part layer-by layer. In a sense, the machine "ink-jet prints" each layer, and hence FDM is also referred to as "3D printing." The physical model is built according to a three-dimensional virtual model that is prepared using CAD software and uploaded to the FDM machine.

CAD/CAM systems have recently been developed and used for the fabrication of partial denture frameworks. One such system uses a "haptic" device, which mimics a waxing tool that is familiar to dental technicians. However, this system generates only a CAD replica in plastic (made by a 3D printer), which requires subsequent extensive processing to obtain a metal partial denture framework. Hence there are still many error-prone steps after the CAD replica is made that can result in a poorly-fitting partial denture framework.

There have been some efforts by major manufacturers of dental materials to make a system to produce a complete (full) denture by 3D printing. The system includes a 3-dimensional scanner for scanning an impression, software for creating a 3-dimensional model of the denture, and the fused deposition modeling equipment for "printing" the denture. However, the materials available to use in 3-dimensional printers are neither as dense nor cross-linked like a normal plastic artificial tooth. Hence a problem remains with the resulting dentures because the denture teeth that are made with available 3D printing plastic materials are not sufficiently wear-resistant.

An alternative approach to denture fabrication is to first make a denture base using a milling machine, which may be computer controlled. Sockets are then milled by the machine into the denture base, and pre-fabricated artificial teeth are placed into the sockets. A problem with this approach is that most of the teeth must be adjusted to some extent to fit within the space required in order for the denture to properly occlude with the opposing arch of the opposing denture or the patients existing opposing teeth. Manual labor is required for the adjustment of teeth; therefore, the potential for errors is introduced into the manufacturing process.

Another problem with this method is that artificial teeth are not consistently sized. They are made from a molding process, with the molds being used for many years. Over the course of use, material from the wall of the mold will wear away, resulting in a mold cavity increasing in size. Hence a tooth made from a mold that has been in service for ten years will be larger than a tooth made when the mold was new. Additionally, molds contain multiple cavities, and the wear is not necessarily uniform. Thus the combination of wear with time and non-uniform wear results in the production of teeth that vary dimensionally within any given tooth size. Moreover, in the denture fabrication marketplace, artificial teeth are returnable for credit. It therefore becomes highly probable that artificial teeth produced 20 years ago from a new mold are in circulation with teeth produced very recently from the same but aged mold having different dimensions.

There is thus a problem in that the dimensional variation of artificial teeth is significant with respect to the dimensions of the sockets formed by the milling machine in which the teeth are to be fitted. The sockets must be milled sufficiently large so as to receive the largest tooth encountered within a given tooth size and shape (i.e. incisor, canine, molar, etc.), and countermeasures taken when the tooth is too small and does not fight tightly into its socket. One countermeasure is to use an acrylic repair resin to secure the teeth into position and to fill the gap(s), of various sizes that may be present around an undersized tooth.

However, this practice is undesirable. Additional labor is required for this step, which is costly and which is likely a manual process which can introduce potential errors to the denture fabrication. The risk of denture tooth "pop-outs" (debonding from the denture base) is more likely because the volume of bonding material is quite small relative to the conventional method of bonding denture teeth, and the bonding surface may be restricted to the circumference of the denture tooth which interfaces with the denture base (and limited bonding of the area of the tooth that opposes the occlusal surface because this area has been adjusted to rest on the "floor" of the socket). In the conventional approach, uncured denture base material surrounds the neck of the teeth and the area of the teeth that oppose the occlusal surface and chemical bonds are formed due to the volume of material and time that the uncured material is allowed to form cross-linked chemical bonds with the artificial teeth.

In addition, like the conventional approach, the patient will not see the final configuration of the denture until the delivery appointment, at which time the patient may reject the denture based on esthetics.

A further reason that "pop-outs" will be more likely with this approach vs. the conventional approach is that the conventional approach relies on a dental technician to adjust each artificial tooth in a way to optimize retention. For example, a dental technician will remove the "glaze" from a denture tooth (shiny and hard surface of the tooth created from a metal mold) to form a better bond with the denture base. Also, "diatoric" holes are often cut into the bottom or side of the tooth, or both, to allow acrylic material to flow in an optimal path to increase the surface area and create mechanical retention in a tooth. The step to provide diatoric holes is yet another processing step that increases cost and introduces the potential for further errors, such as artificial tooth fracture.

Yet another approach to denture fabrication is to mill blocks of polymerized plastic to make a complete denture. This process involves milling a block of pink methacrylate material as the denture base (including the gingiva surrounding the teeth). The teeth are then milled from a single piece of plastic. Lastly, the pink denture base and the milled teeth are cemented together. This technique is useful to make an immediate denture for temporary use, such as after a tooth-extraction for use while the gums heal. However, it is not suitable for long-term dentures because the artificial teeth made in this manner look unaesthetic. Natural dentition has subtle color (hue) variations as well as translucencies, color volume and defects. These effects are built-into most artificial teeth which are generally made in 2 to 4 layers of overlapping material (plastic or porcelain), each layer having different shades and levels of translucency. These layers create a natural effect of tooth structure, especially in anterior (front) teeth which often display "mamelons" and translucent incisal edges.

Artificial teeth that have an aesthetically pleasing appearance are generally made of highly cross-linked polymethylmethacrylate plastic, but may also be made of porcelain. Such artificial teeth are made with a series of metal dies in which the teeth are formed one-layer at a time. When all of the layers are completed, the "green" tooth is then heated to polymerize the plastic (or super-heated in the case of porcelain teeth). The heating process completes the cross-linking process in plastic teeth to make the teeth resistant to wear from the forces of mastication. This process is not compatible with the above overall denture fabrication process in which the full set of teeth are milled from a single piece of plastic and bonded to the milled denture base.

In summary, there remains a need for a method and apparatus for fabricating a denture at low cost in a minimal number of steps and with minimal manual labor, and preferably at a single manufacturing station. A denture made by any such method and apparatus must be made with sufficient precision so as to fit the patient properly, and have teeth that are firmly retained, wear resistant, and aesthetically pleasing.

SUMMARY

In accordance with the present disclosure, the problem of fabricating a denture at low cost in a minimal number of steps and with minimal manual labor is solved by using a block of denture base material as a receptacle for molding the teeth. The block of denture base material is milled by a milling machine or other material removal device to create a mold for the teeth. Fluid tooth material is dispensed into the mold and cured into solid tooth material. The combination of cured solid tooth material in the mold and denture base material are milled to form the denture. More specifically, in certain embodiments, the problem of making a denture comprised of a base and a plurality of teeth joined to the base is solved by forming a first cavity in a block of a denture base material, the first cavity formed to match the contour of natural teeth as arranged on maxillae or on a mandible; filling the first cavity with a first fluid synthetic tooth material and solidifying the first fluid synthetic tooth material into a first solid synthetic tooth material; removing a portion of the first solid synthetic tooth material to form the plurality of teeth; and removing a portion of the block of denture base material to form the denture base. The steps of the method may be implemented by a computer.

The method may further comprise heat treating the denture base and plurality of teeth. Solidifying (polymerization in certain embodiments) the first fluid synthetic tooth material may be performed by heating and/or irradiating the first fluid synthetic tooth material. The heating may be provided by an exothermic chemical reaction in the fluid synthetic tooth material (i.e., self heating), or by an external heat source. In instances where it is desired to make a temporary denture for trial fitting purposes, the first solid synthetic tooth material may be a wax.

The denture may be defined by a digital three-dimensional model. In such an embodiment, forming the first cavity may be performed based upon data from the three-dimensional model. Additionally, the removing a portion of the first solid synthetic tooth material to form the plurality of teeth and the removing a portion of the block of denture base material to form the denture base may be performed to produce the denture having the dimensions defined in the three-dimensional model.

In certain embodiments, the plurality of teeth may be formed by molding two or more fluid synthetic tooth materials. In such embodiments, the denture fabrication method comprises forming a first cavity in a block of a denture base material as recited above; filling the first cavity with a first fluid synthetic tooth material and solidifying the first fluid synthetic tooth material into a first solid synthetic tooth material; forming a second cavity by removing a portion of the first solid synthetic tooth material, the second cavity being formed to match the contour of natural teeth as arranged for the contour of the first cavity; filling the second cavity with a second fluid synthetic tooth material and solidifying the second fluid synthetic tooth material into a second solid synthetic tooth material; removing a portion of the second solid synthetic tooth material to form the plurality of teeth; and removing a portion of the block of denture base material to form the denture base.

The denture base and plurality of teeth may be heat treated after formation in order to fully cross-link the polymers of the base and teeth. Solidifying the second fluid synthetic tooth material may be performed by external heating, self-heating and/or irradiating the second fluid synthetic tooth material. As recited above, the denture may be defined by a digital three-dimensional model, in which case, forming the first cavity and forming the second cavity may be performed based upon data from the three-dimensional model. Additionally, removing a portion of the second solid synthetic tooth material to form the plurality of teeth and the removing a portion of the block of denture base material to form the denture base may be performed to produce the denture having the dimensions defined in the three-dimensional model.

The method may be further comprised of filling the second cavity with a third fluid synthetic tooth material, causing the third fluid synthetic tooth material to solidify into a third solid synthetic tooth material, and removing a portion of the third solid synthetic tooth material to re-form the second cavity, prior to filling the second cavity with the second fluid synthetic tooth material.

The second solid synthetic tooth material may differ from the first solid synthetic tooth material. In certain embodiments, the second solid synthetic tooth material may be synthetic translucent tooth enamel material.

The method may be used to make a trial denture in which the first solid synthetic tooth material is a wax. The trial denture may then be fitted to a patient, and final adjustments made to the positions of the relatively soft wax synthetic teeth and/or base. The fitted trial denture may then be scanned in three dimensions to obtain scanned denture data, which may then be used to produce the digital three-dimensional model. The 3D model may then be used by a computer to control the denture-making apparatus to produce the final denture as described herein.

The method may be used to make a trial denture in which the denture base is made from a suitable material such as methacrylate polymer, typically of a pink flesh-tone color. Sockets are formed in the denture base by a milling machine, which are then filled by pink-colored wax. Then a portion of the wax and denture base is removed by the milling machine in order to create a void that can be filled by fluid synthetic tooth material made from tooth-colored methacrylate. The sockets made from wax are preferred because they enable a dentist to adjust the position of the teeth if necessary in order to optimize occlusion or esthetics. Dentists are accustomed to making adjustments to trial dentures, so this method is consistent with present practice. In addition, the teeth can be made from multiple layers of tooth-colored methacrylate or other suitable polymer so that the trial denture will look exactly like the finished denture, thereby increasing the likelihood of patient acceptance at the final delivery appointment.

Also according to the present disclosure, an apparatus for making a denture comprised of a base and a plurality of teeth joined to the base is provided. The apparatus is comprised of a material holding fixture, a material removal device, and a first fluid synthetic tooth material delivery device. The material removal device is contactable with a block of denture base material held by the fixture so as to remove denture base material and form a first mold cavity in the block for receiving the first fluid synthetic tooth material. The first mold cavity is formed to match the contour of natural teeth as arranged on maxillae or on a mandible. The first fluid synthetic tooth material delivery device is configured to deliver the first fluid synthetic tooth material into the first mold cavity.

The apparatus may be further comprised of a fluid-to-solid tooth material curing device configured to cure the first fluid synthetic tooth material in the first mold cavity into first solid tooth material. The material holding fixture and material removal device are movable with respect to each other so as to enable the material removal device to remove denture base material from the block and first solid tooth material in the first mold cavity so as to form the denture base and at least a portion of the plurality of teeth.

The apparatus may be further comprised of a second fluid synthetic tooth material delivery device configured to deliver the second fluid synthetic tooth material into a second mold cavity formed by the material removal device removing a portion of the first solid tooth material. In such an embodiment, a fluid-to-solid tooth material curing device may be configured to cure the second fluid synthetic tooth material in the second mold cavity into second solid tooth material. Additionally, the material holding fixture and material removal device may be movable with respect to each other so as to enable the material removal device to remove second solid tooth material in the second mold cavity so as to form at least a portion of the plurality of teeth.

The apparatus may be further comprised of a third fluid synthetic tooth material delivery device configured to deliver the third fluid synthetic tooth material into a third mold cavity formed by the material removal device removing a portion of the first solid tooth material. In such an embodiment, a fluid-to-solid tooth material curing device may be configured to cure the third fluid synthetic tooth material in the third mold cavity into third solid tooth material. Additionally, the material holding fixture and material removal device may be movable with respect to each other so as to enable the material removal device to remove third solid tooth material in the third mold cavity so as to form at least a portion of the plurality of teeth.

Also according to the present disclosure, a denture comprised of a base and a plurality of teeth joined to the base is provided. The teeth are comprised of a posterior region of a first solid synthetic tooth material and an anterior region of a second solid synthetic tooth material. The second solid synthetic tooth material preferably has the appearance to an observer of natural teeth. The teeth may be further comprised of a third solid synthetic tooth material in an interior region between the first solid synthetic tooth material and the second solid synthetic tooth material.

As a result of the invention, certain benefits in the manufacturing of dentures are realized. The requirement for skilled manual labor in fabrication is virtually eliminated. The opportunity to use computer control over all steps of fabrication also eliminates many errors, as well as making the process highly versatile. Via the use of software, a dental professional may create any shape and color of teeth to match the clinical and aesthetic needs of the patient, and the method and apparatus can be employed to make them to order. In addition, a dentist can show the patient a digital photo of his/her face with his/her new dentures, before the start of the fabrication process, thereby increasing the likelihood of patient acceptance of the denture at the delivery appointment. The manual expertise formerly required for tooth set-up in the denture is no longer needed, because such set-up can be predetermined using CAD software, and a digital three dimensional model of the denture uploaded to the computer-controlled fabrication apparatus.

Additionally, the need for a dental lab to maintain a large stock of denture teeth is also eliminated. This is a significant cost savings, in that some dental labs maintain over $100,000 worth of teeth in their inventory in order to be able to timely satisfy incoming orders. In addition, handling costs of a large tooth inventory can be eliminated: shipping costs, ordering and stocking/retrieving costs, risk of theft/damage, cost of handling returns of partially used sets of teeth, etc. Furthermore, the shades, shapes, anatomy, imperfections, translucency, etc. of the teeth can be custom-made for each denture.

If it is desirable to fabricate a temporary "try-in" denture with wax teeth for a test fit before fabricating a long-term denture, the method and apparatus can be used to fabricate the try-in denture as described previously, but using a wax material for the teeth. A methacrylate or other suitable denture base material is milled to form a cavity whereby tooth-colored wax is placed in the cavity to form wax teeth. Because the synthetic teeth material is wax, in the dental office, a dentist can fit the try-in denture to the patient, and make final adjustments to optimize its fit and aesthetics. Then the final-adjusted try-in denture can be scanned in 3D and digitally compared to the original "wax try-in denture" and/or used as the source of a new three-dimensional denture model to be used in manufacturing the long term denture. In that manner, the final denture will have optimal fit to the patient, with only one fitting session needed with him/her before the final denture is delivered and fitted.

If it is desirable to fabricate a temporary "try-in" denture with resin teeth for a test fit before fabricating a long-term denture, the method and apparatus can be used to fabricate the try-in denture as described previously. A methacrylate denture base material is milled to form sockets where the teeth will be fabricated. The sockets are subsequently filled with moldable wax. Then the apparatus mills a cavity whereby tooth-colored resin is placed in the cavity to form the teeth. Because the synthetic teeth material is resin in a socket made of wax, in the dental office, a dentist can fit the try-in denture to the patient, and make final adjustments to optimize its fit and aesthetics. Additionally, the patient can see the color and translucency of the final denture teeth before the final denture is made, thereby increasing the likelihood of patient acceptance at the final appointment. Then the final-adjusted try-in denture can be scanned in 3D and digitally compared to the original "wax try-in denture" and/or used as the source of a new three-dimensional denture model to be used in manufacturing the long term denture. In that manner, the final denture will have optimal fit to the patient, with only one fitting session needed with him/her before the final denture is delivered and fitted.

It is also noted that in manufacturing a denture according to the instant method, the artificial teeth are chemically bonded to the denture base on all surfaces which the artificial teeth interface with the denture base. This significantly reduces the likelihood of the artificial teeth detaching from the denture base (referred as a "pop-out"), and the formation of dark demarcation lines around the junction of the artificial teeth and artificial gingiva due to bacterial growth. (The latter problem is often found in dentures made with porcelain artificial teeth because there is no chemical bond between the denture base and the teeth.) Accordingly, the artificial teeth will look more natural.

BRIEF DESCRIPTION OF THE DRAWINGS

The present disclosure will be provided with reference to the following drawings, in which like numerals refer to like elements, and in which.

Figure 1A:
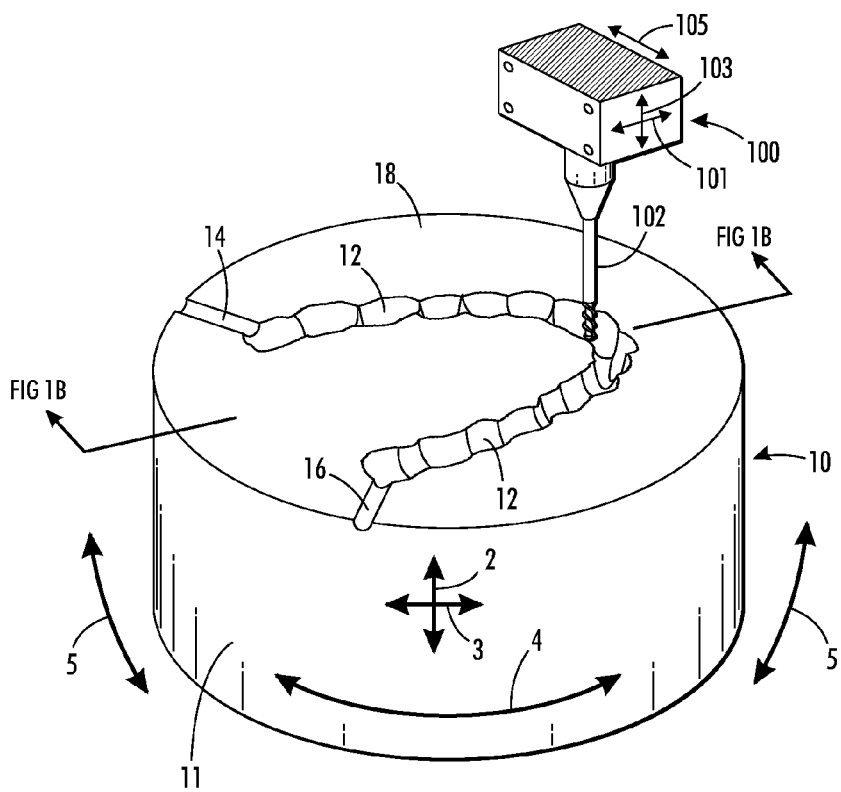
FIG. 1A is a perspective view of a block of denture base material having a first cavity being formed therein according to the method and apparatus of the present disclosure.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements.

In accordance with the present disclosure, there are provided a method and an apparatus for making a dental prosthesis, such as a denture, by using a block of denture base material as a receptacle for molding the teeth of the denture. The block of denture base material is milled by a milling machine or other material removal device to create a mold for the teeth, dispensing liquid tooth material in the mold and curing it into solid tooth material, and milling the combination of cured solid tooth material in the mold and denture base material to form the denture.

Figure 1B:
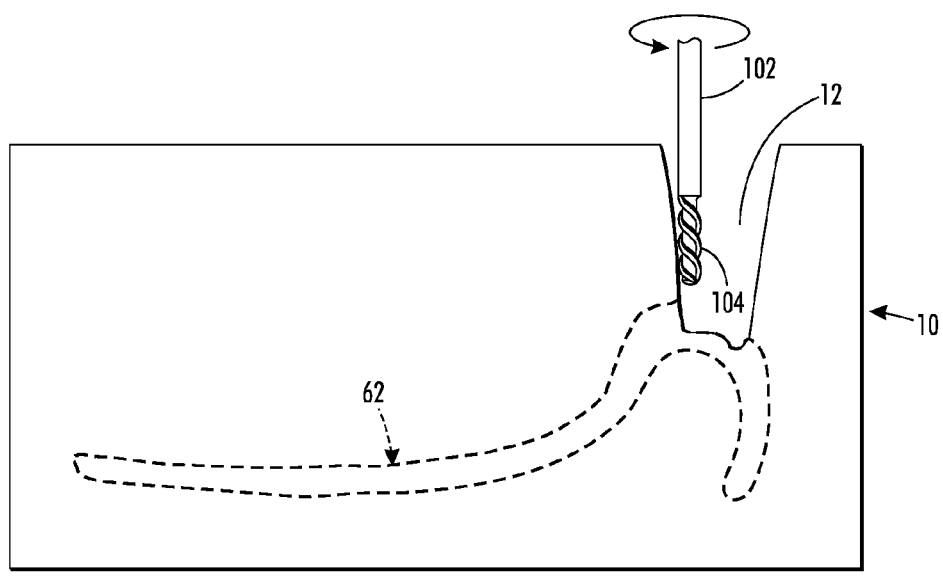
FIG. 1B is a cross-sectional view of the block and apparatus of FIG. 1A, taken along line 1B-1B of FIG. 1A.

Turning first to FIGS. 1A and 1B, a block 10 of denture base material is shown in the process of having a first cavity 12 being formed therein. The first cavity 12 is formed to match the generally U-shaped contour of natural teeth as arranged on maxillae or on a mandible, for reasons that will become apparent subsequently.

The first cavity may be formed by using a mill, a portion of which is indicated by numeral 100, comprising a milling bit 102 having side and/or end cutting teeth 104. The overall fabrication apparatus includes a combination of rotation and translation means for the block of material and for the milling bit 102 so that they are movable with respect to each other along and around multiple axes, as is known in the machining arts. For example, the block 10 may be linearly movable along orthogonal axes 2 and 3 and along a third axis orthogonal to axes 2 and 3, and rotatable around those axes as indicated by arcuate arrows 4 and 5. The milling bit 102 may be linearly movable along orthogonal axes 101, 103, and 105, and rotatable around these axes. Thus the block 10 and milling bit 104 are movable with respect to each other over a full range of motion so as to enable the milling of the intricate shapes of cavities therein, and also the intricate shapes of the denture base and artificial teeth as will be described subsequently. It is noted that for the sake of simplicity of illustration, the movable fixturing for the block 10 of denture base material and the motion control devices for the milling bit 102 are not shown.

The mill 100 is preferably controlled by a computer, i.e. the mill 100 is a CNC (computer numerically controlled) mill. The mill 100 may include a turret and tool changer (not shown), so that multiple tool bits 102 may be used in milling the cavities in the block 10 and the final denture base and artificial teeth of the denture. Larger tool bits may be used for fast removal of large portions of material, and smaller tool bits may be used for the finishing of intricate shapes of the cavities, final denture base and artificial teeth. As an example, the milling machine including the movable block fixture may be a Model DWX mill manufactured by the Roland DGA Corporation of Irvine, Calif.

It is not required that the removal material device be a milling machine. Other material removal devices/processes are contemplated, such as laser ablation, water jet machining, and the like.

Figure 2A:
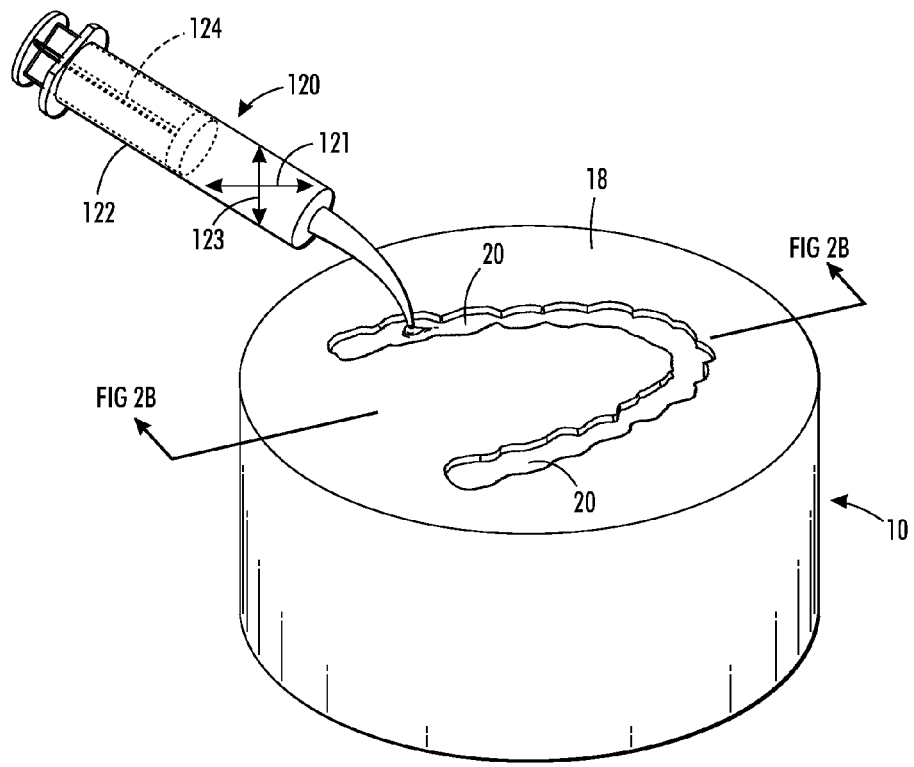
FIG. 2A is perspective view of a fluid dispensing device delivering first fluid synthetic tooth material into the cavity formed in the step depicted in FIG. 1A.

When the forming of the first cavity 12 in the block 10 of denture base material is complete, the cavity 12 is filled with a first fluid synthetic tooth material by a fluid material delivery device. In certain embodiments, as shown in FIG. 2A, the material delivery device 120 may be a syringe 122 that contains first fluid synthetic tooth material 20. The syringe 122 may be part of a syringe pump (not shown), which may include means (not shown) for controlling the displacement of the syringe plunger 124, and means (not shown) for moving the syringe 122 relative to the block 10 along orthogonal axes 121 and 123, and a third axis orthogonal to them. In that manner, the syringe 122 may be traversed along the U-shape of the cavity 12 as it dispenses first fluid synthetic tooth material therein.

Other means for delivering the fluid synthetic tooth material may be suitable, such as positive displacement metering pumps (not shown), which may include on/off valving and other delivery control devices (not shown). In other embodiments, the fluid synthetic tooth material can be delivered under pressure into the void in the denture base wherein the denture base is encapsulated within a flask or vacuum chamber on other restraining device that will enable complete filling of all voids created in the denture base. In certain embodiments, the means for delivering the fluid synthetic tooth material to the cavity may be an apparatus that delivers fluid materials as performed in fused deposition modeling, also known as "3D printing" as described previously herein.

Referring back to FIG. 1A, in addition to milling the U-shaped cavity corresponding to the shape of natural teeth, one or more troughs (known in the art as "sprues") may be milled in the top surface of the block 10 of denture base material. The sprues 14 and 16 extend from the cavity 12 to the side wall 11 of the block 10. Alternatively, sprues (not shown) may be drilled through the side wall 11 slightly below the top surface of the block to the cavity 12.

In such configurations, after the forming of the cavity 12 and sprues 14 and 16 or sub-surface sprues (not shown), the block 10 may be placed in a container (known in the art as a "flask"), and the fluid synthetic tooth material 20 may be injected into the cavity 12 through the sprues in a manner analogous to injection molding. As noted above, vacuum may be used to facilitate flow into or through the cavity 12.

Figure 2B:
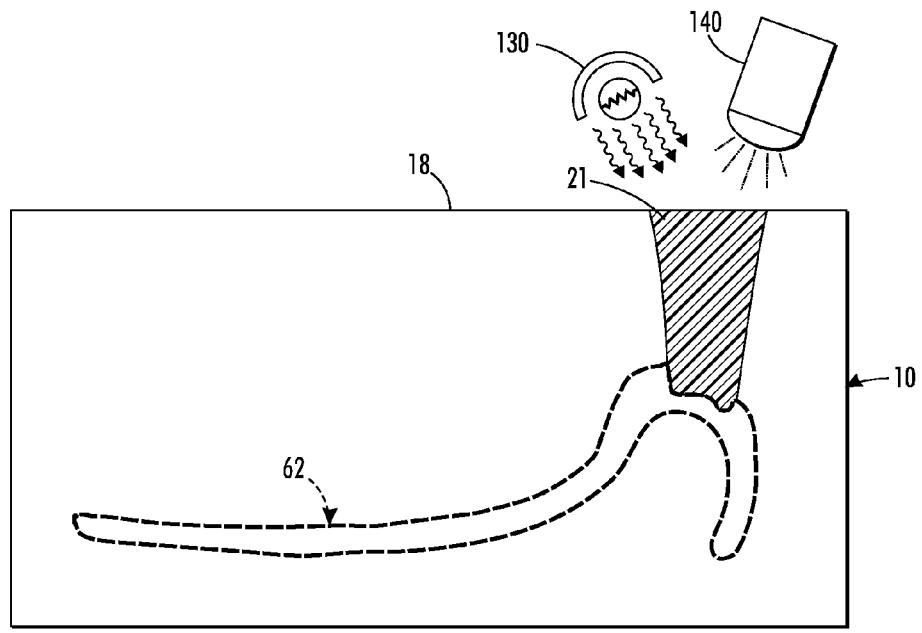
FIG. 2B is a cross-sectional view of the block of FIG. 2A, taken along line 2B-2B of FIG. 2A, showing means for solidifying the first fluid synthetic tooth material in the cavity in the block of denture base material.

Referring now to FIG. 2B, after the cavity 12 has received first fluid synthetic tooth material 20, such fluid material is solidified into first solid synthetic tooth material 21. (It is noted that "synthetic solid tooth material" as recited herein is meant to indicate a tooth material other than solid tooth material that is produced by the natural biological process of tooth formation.) The solidification process may be the result of the formulation of the first fluid synthetic tooth material, which may be a "self-curing" material such as methyl methacrylate resin.

In certain embodiments, the solidification (or "curing") of the first fluid synthetic tooth material 20 may be partially or wholly caused by the application of heat, such as by an infrared heater 130 and/or a convection heater (not shown). In other embodiments, the solidification of the first fluid synthetic tooth material 20 may be partially or wholly caused by irradiating the first fluid synthetic tooth material 20 with a light 140. In such embodiments, the first fluid synthetic tooth material 20 may be formulated as a light sensitive material which may be cured by the application of high-energy radiation, such as ultraviolet light. Alternatively, the light may be visible light, or the light may be infrared light which provides heating of the fluid synthetic tooth material 20.

Figure 7:
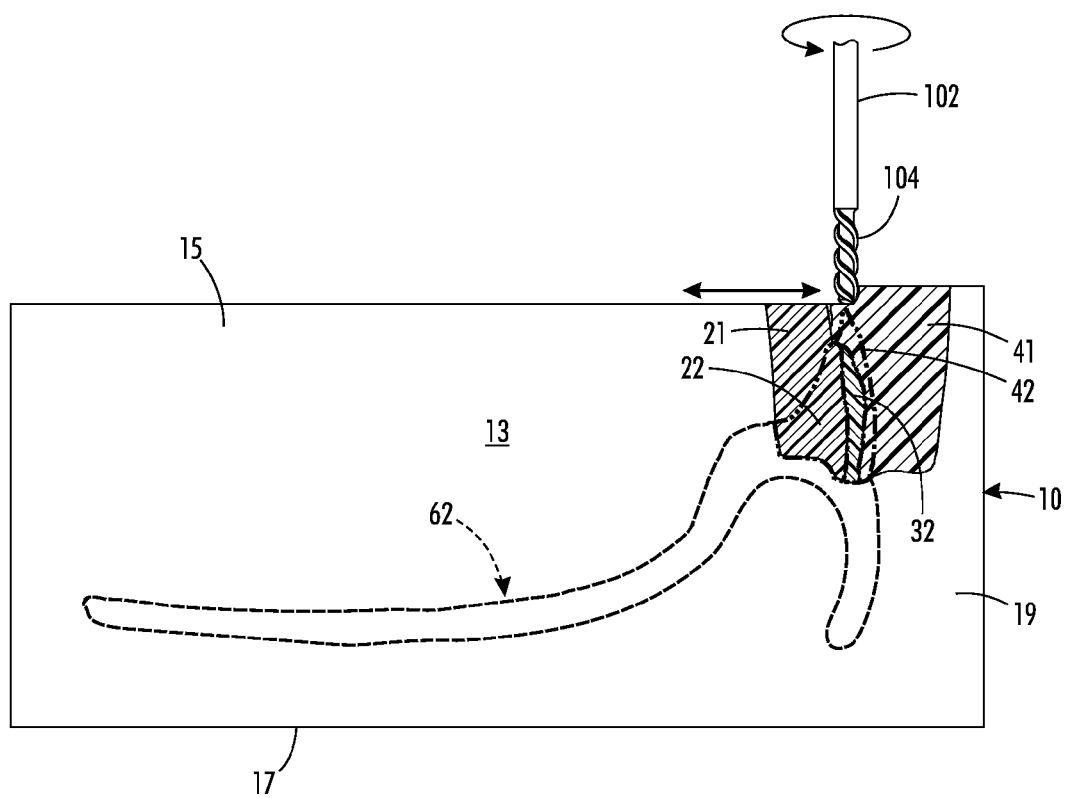
FIG. 7 is a cross-sectional view of the block and first, second, and third solid synthetic tooth materials, showing the beginning of the final material removal step to form the finished denture.
Figure 8A:
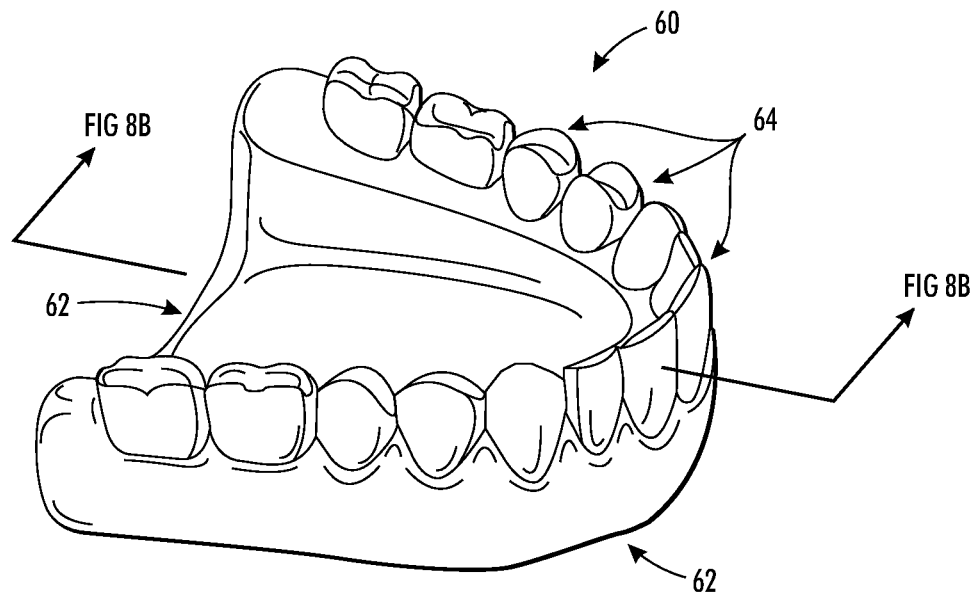
FIG. 8A is a perspective view of a finished denture made according to the method and apparatus of the present disclosure.
Figure 8B:
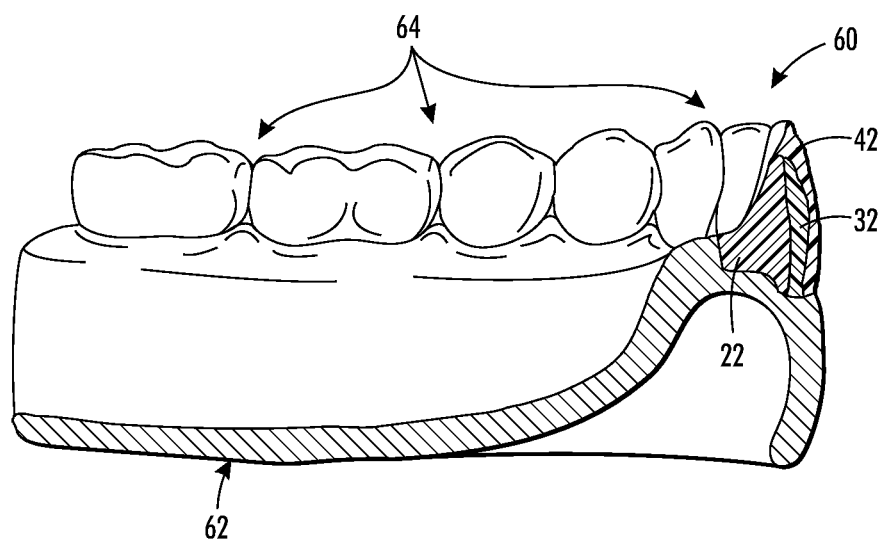
FIG. 8B is cross-sectional view of the denture of FIG. 8A, taken along the line 8B-8B of FIG. 8A.

In certain embodiments, a portion of the first solid synthetic tooth material 21 may then be removed to form the plurality of teeth, and a portion of the block 10 of denture base material may be removed to form the denture base, thus forming the overall finished denture 60 (FIGS. 8A and 8B). Referring to FIG. 7, the milling bit 102 is traversed over and/or around the block 10, optionally with both the block 10 and the bit 102 moved relative to each other. Denture base material 13 is removed from the upper region 15, the lower region 17, and the lateral region 19 of the block 10, leaving behind the denture base 62. To facilitate material removal, the fixturing for the block 10 may be provided with means (not shown) for inverting the block 10 relative to the mill bit 102.

Additionally, the first solid synthetic tooth material 21 is removed by the milling bit 102 as required to form the plurality of teeth 64. It is noted that in FIG. 8B, the synthetic teeth 64 shown in cross-section are shown as comprising first solid synthetic tooth material 22, second solid synthetic tooth material 32, and third solid synthetic tooth material 42. The fabrication of teeth 64 may include a second solid synthetic tooth material 32, and further include a third solid synthetic tooth material 42 as will be explained subsequently herein.

However, the finished denture 60 may have the plurality of teeth 64 made of only the first solid synthetic tooth material 22, but occupying the entire tooth volume/shape of the teeth 64 formed by tooth materials 22, 32, and 42 in FIG. 8B. One circumstance where it may be desirable to make a denture 60 having teeth 64 of only a first solid synthetic tooth material 22 is when a denture 60 is needed that is of minimal cost. Another circumstance is where it is desirable to make a temporary "try-in" denture for a test fit before fabricating a long-term denture. A solid but formable wax material may be used as the teeth 64 formed therein. Because the first synthetic tooth material 22 are made of wax in such circumstance, in the dental office, a dentist can fit the try-in denture to the patient, and make final adjustments to optimize its fit and aesthetics. Then the final-adjusted try-in denture can be scanned in three dimensions and digitally compared to the original "wax try-in denture" and/or used as the source of a new three-dimensional denture model to be used in manufacturing the long term denture. In that manner, the final denture will have optimal fit to the patient, with only one fitting session needed with him/her before the final denture is delivered and fitted.

In certain preferred embodiments, the teeth 64 of the finished denture may include second solid synthetic tooth material 32, and third solid synthetic tooth material 42. Referring to FIG. 8B, the second solid tooth material 32 may be a tooth colored material with a white or slightly off-white coloration. The third solid synthetic tooth material 42, which may entirely cover the second solid synthetic tooth material 32 and extend upwardly past such material 32, may be a translucent material. By so choosing such second and third solid synthetic tooth materials 32 and 42, the appearance of natural teeth is best replicated in the finished denture 60. It is also noted that in such a configuration, the appearance of the first solid synthetic tooth material 22 being "natural" is less important, because the first solid synthetic tooth material 22 is located on the posterior region of the teeth 64, i.e., on the inside of the teeth 64 proximate to the tongue, and is thus generally not visible to others, except a dentist or other clinician performing dental tasks or examinations.

The fabrication of the denture 60 comprising second synthetic tooth material 32 and third solid synthetic tooth material 42 will now be described. Referring again to FIG. 3, after the first fluid synthetic tooth material 20 has been cured into first solid synthetic tooth material 21 (FIG. 2), a second cavity 23 is formed by removing a portion of the first solid synthetic tooth material 21. The second cavity 23 is formed to match the contour of natural teeth as was done for the contour of the first cavity 12 (FIG. 1A). It is noted that in FIG. 2B and FIG. 3, the filling of the cavity 12 with first liquid synthetic tooth material 20 is shown as completely filling the cavity 12 to the top surface 18 of the block 10 prior to its curing into first solid synthetic tooth material 21. However, it is not necessary to fill the cavity 12 completely; instead, the cavity 12 needs to only be filled to the highest point of the first solid tooth material 22 that is going to remain as part of the synthetic teeth 64. The same principle applies with respect to the filling of cavities that receive second fluid synthetic tooth material 30 (FIG. 4A) and third fluid synthetic tooth material (not shown).

Figure 4A:
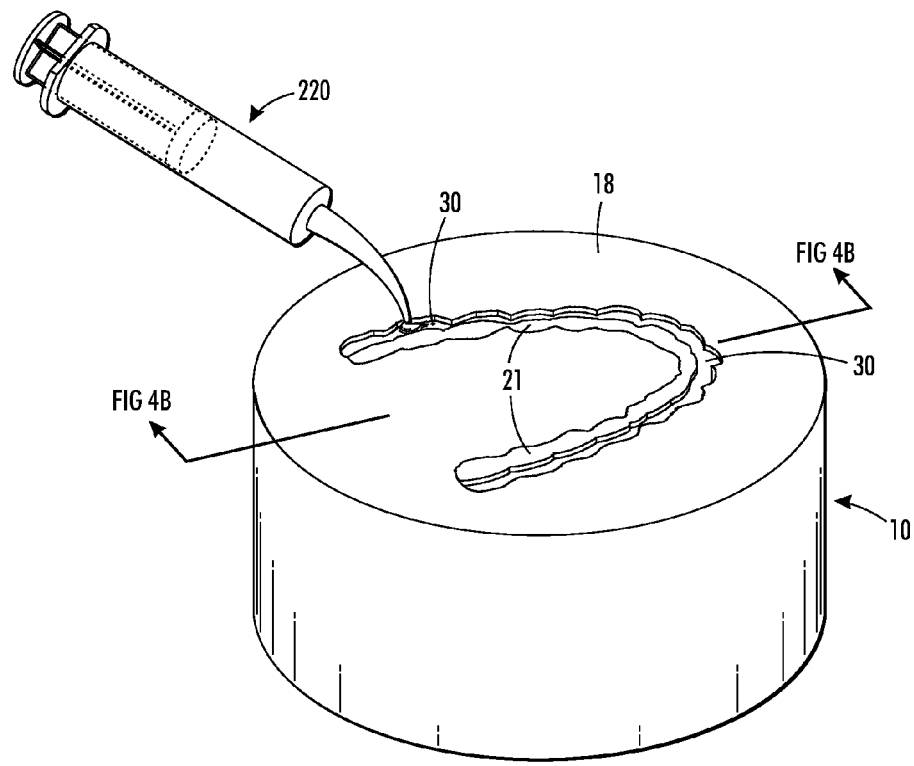
FIG. 4A is perspective view of a fluid dispensing device delivering second fluid synthetic tooth material into the cavity formed in the step depicted in FIG. 3.
Figure 4B:
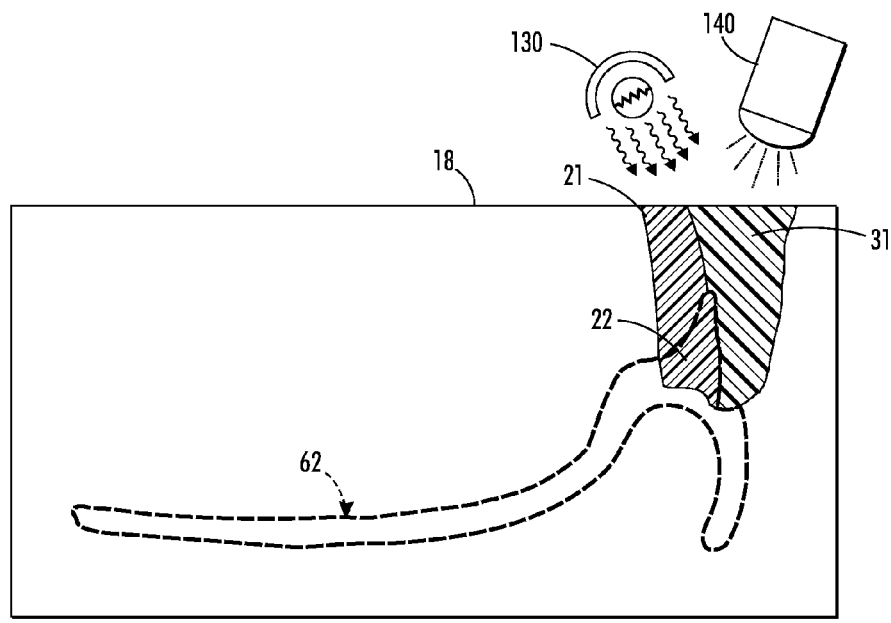
FIG. 4B is a cross-sectional view of the block of FIG. 4A, taken along line 4B-4B of FIG. 4A, showing means for solidifying the second fluid synthetic tooth material in the second cavity in the block.

Referring to FIG. 4A, the second cavity 23 receives a second fluid synthetic tooth material 30, from a suitable source such as e.g., syringe 220. Referring to FIG. 4B, the second fluid synthetic tooth material 30 is solidified into a second solid synthetic tooth material 31. The second fluid synthetic tooth material 30 may be solidified by the use of a heater 130, or a light 140, or material 30 may be self-curing, all as described previously with respect to first fluid synthetic tooth material 20.

In certain embodiments, a portion of the second solid synthetic tooth material 31 may then be removed to form the plurality of teeth 64, and a portion of the block 10 of denture base material may be removed to form the denture base, thus forming the overall finished denture 60 of FIGS. 8A and 8B as described previously. In such embodiments, the teeth 64 are made of first solid synthetic tooth material 22 forming a posterior region of the teeth 64, and second solid synthetic tooth material 32 forming the anterior region of the teeth 64. The second solid synthetic tooth material 32 may occupy the additional volume occupied by third solid synthetic tooth material 42 shown in FIG. 8B.

Figure 3:
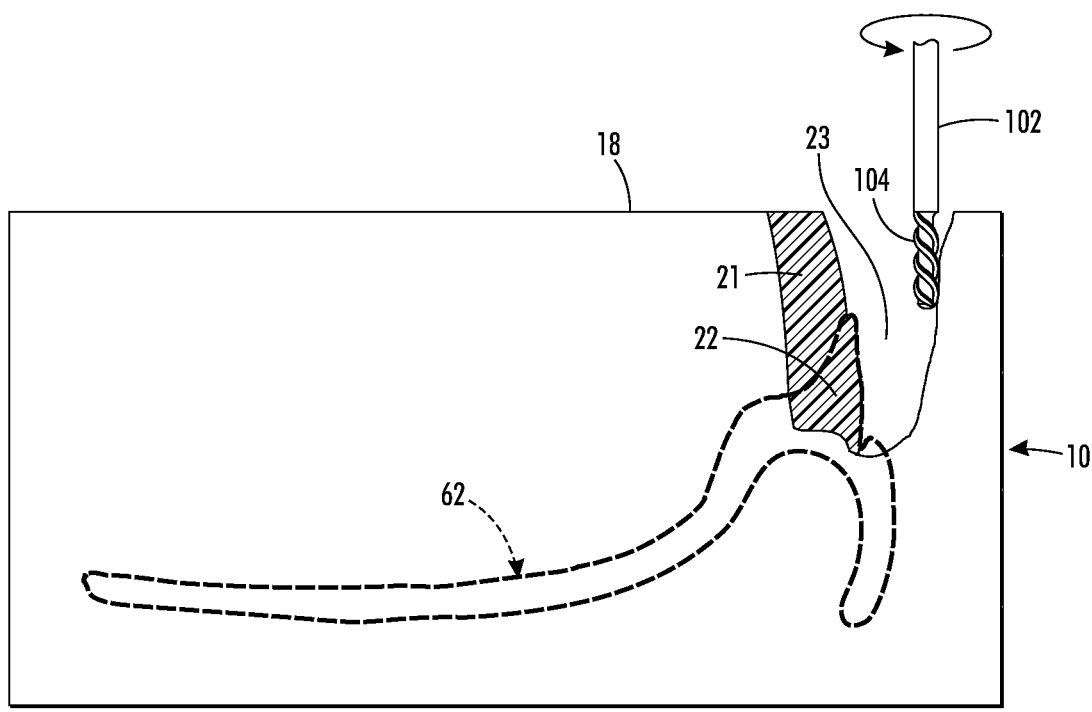
FIG. 3 is a cross-sectional view of the block of denture base material and first solid tooth material as depicted in FIG. 2B, but showing a material removal device removing a portion of the first solid tooth material to form a second cavity in the block.
Figure 5:
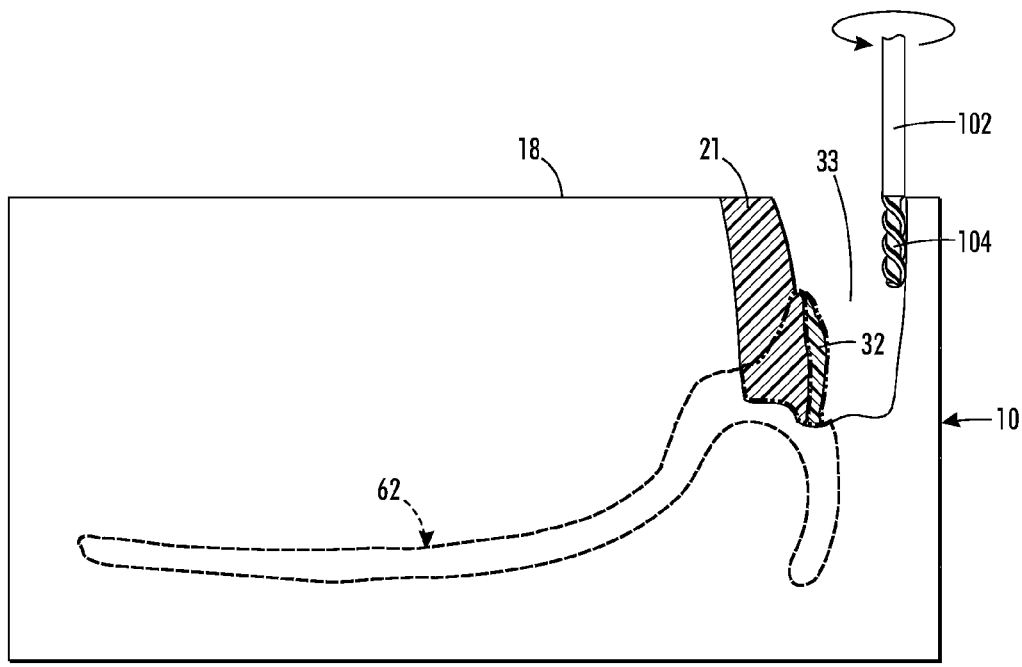
FIG. 5 is a cross-sectional view of the block of denture base material and first and second solid tooth material as depicted in FIG. 4B, but showing a material removal device having removed a portion of the second solid tooth material to form a third cavity in the block.

However, for reasons described previously directed to having the most natural appearing and aesthetically pleasing teeth 64, it is preferred to fabricate such teeth 64 to be comprised of the third solid synthetic tooth material 42. This is best understood with reference to FIGS. 5-7. Referring first to FIG. 5, after the second fluid synthetic tooth material 30 has been cured into second solid synthetic tooth material 31 (FIG. 4B), a third cavity 33 is formed by removing a portion of the second solid synthetic tooth material 31. The second cavity 33 is formed to match the contour of natural teeth as was done for the contours of the first and second cavities 12 and 23 (FIG. 1A and FIG. 3).

Figure 6:
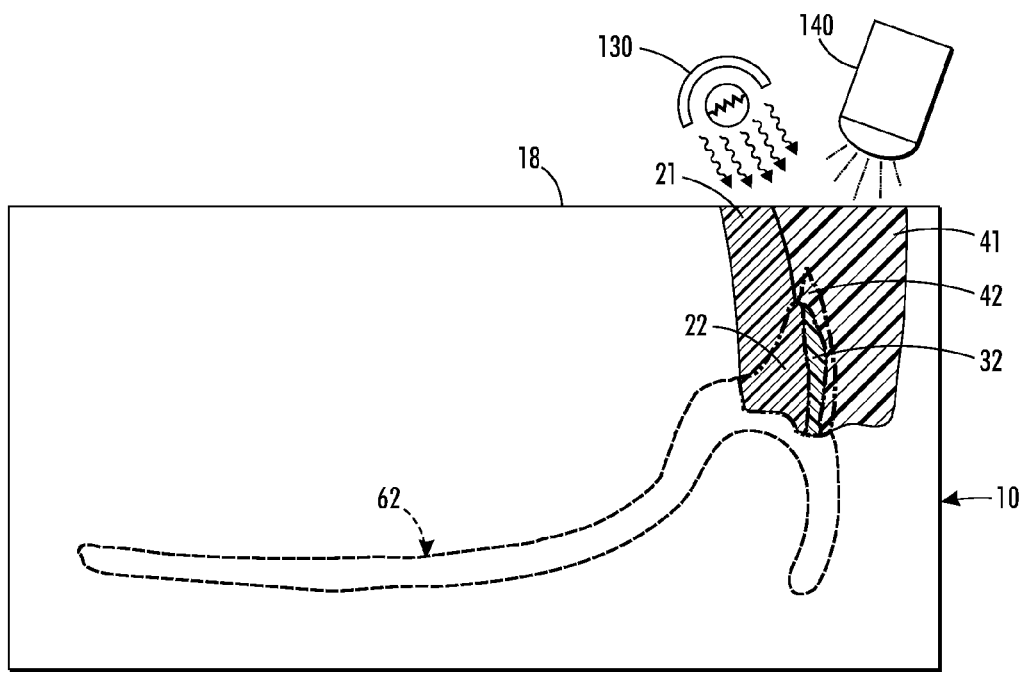
FIG. 6 is a cross-sectional view of the block after the dispensing of a third fluid synthetic tooth material into the cavity formed in FIG. 5, showing means for solidifying the third fluid synthetic tooth material in the cavity.

The third cavity 33 receives a third fluid synthetic tooth material from a suitable source such as a syringe (not shown). Referring to FIG. 6, the third fluid synthetic tooth material is solidified into a third solid synthetic tooth material 41. The third fluid synthetic tooth material may be solidified by the use of a heater 130, or a light 140, or the third fluid synthetic tooth material may be self-curing, all as described previously with respect to first fluid synthetic tooth material 20.

Referring to FIGS. 7-8B, with first, second, and third solid tooth materials 22, 32, and 42 provided, the finished denture 60 may be completed. As described previously, the milling bit 102 is traversed over and/or around the block 10, optionally with both the block 10 and the bit 102 moved relative to each other. Denture base material 13 is removed from the upper region 15, the lower region 17, and the lateral region 19 of the block 10, leaving behind the denture base 62. Additionally, first solid synthetic tooth material 21 and third solid synthetic tooth material 41 are removed by the milling bit 102 as required to form the plurality of teeth 64.

In summary, the instant method may be used to produce a denture comprising a denture base material and synthetic teeth. The synthetic teeth may be comprised of one, two, or three solid synthetic tooth materials. The synthetic teeth may be made of a single tooth material with differing shades and color opacity. Alternatively, the teeth may be comprised of a posterior region of a first solid synthetic tooth material and an anterior region of a second solid synthetic tooth material. The second solid synthetic tooth material preferably has the appearance to an observer of natural teeth, and may be a translucent material. The teeth may be further comprised of a third solid synthetic tooth material in an interior region between the first solid synthetic tooth material and the second solid synthetic tooth material. The third solid synthetic tooth material may have the color of natural teeth. When used in combination with a second solid tooth material that is translucent, more natural looking artificial teeth are provided. In certain embodiments, the solid synthetic tooth materials are polymer materials. More particularly, in certain embodiments, the solid synthetic tooth materials may be methylmethacrylate polymer.

In certain embodiments, the fluid synthetic tooth materials may contain solid particles and/or fibers, such as pigments for coloration, and/or particles or fibers to improve wear resistance and structural strength of the artificial teeth. The fluid synthetic tooth materials may be formulated as liquid/solid dispersions. The fluid synthetic tooth materials may be formulated as hot melt materials that are delivered into the cavities in a molten state and then solidify.

The instant method may further comprise heat treating the denture base and plurality of teeth after their formation. Such heat treatment may improve cross-linking of the artificial teeth, thereby improving their strength and wear resistance, and it may also improve the chemical bond of the teeth to the denture base. The improved chemical bond is believed to decrease the likelihood of the artificial teeth detaching from the denture base (referred as a "pop-out"), and the formation of dark demarcation lines around the junction of the artificial teeth and artificial gingiva due to bacterial growth. (The latter problem is often found in dentures made with porcelain artificial teeth of the current art, because there is no chemical bond between the denture base and such porcelain teeth).

The method may further comprise a "touch-up" step, in which any small imperfections are removed with a small high-speed milling tool. In a final step, the denture base and teeth may be polished using a polishing lathe to a smooth finish to maximize comfort for the wearer, to minimize bacterial growth on the surfaces, and to maximize aesthetic appearance.

In addition to the instant method, there is also provided an apparatus for making a denture comprised of a base and a plurality of teeth joined to the base. In general, the apparatus may include a combination of certain hardware operated by a computer that includes certain software. The method and apparatus may be referred to in general as a CAD-CAM (Computer Aided Design/Computer Aided Manufacturing) system. Referring to FIGS. 1A-7, the apparatus may include a material holding fixture (not shown), a material removal device, and a first fluid synthetic tooth material delivery device. The material removal device is contactable with a block of denture base material held by the fixture so as to remove denture base material and form a first mold cavity in the block for receiving the first fluid synthetic tooth material. The material removal device may be a mill, such as mill 100 comprising mill bit 102 of FIG. 1A. The first fluid synthetic tooth material delivery device, such as syringe 120, is configured to deliver the first fluid synthetic tooth material 20 into the first mold cavity 12.

The apparatus may be further comprised of a fluid-to-solid tooth material curing device configured to cure the first fluid synthetic tooth material 20 in the first mold cavity 12 into first solid tooth material 21. The fluid-to-solid tooth material curing device may be a heater 130 and/or a light 140, such as an ultraviolet light.

The material holding fixture (not shown) and material removal device 100 are movable with respect to each other so as to enable the material removal device 100 to remove denture base material 13 from the block 10 and first solid tooth material 21 in the first mold cavity 12 so as to form the denture base 62 and at least a portion of the plurality of teeth 64.

The apparatus may be further comprised of a second fluid synthetic tooth material delivery device, such as syringe 220, configured to deliver the second fluid synthetic tooth material 30 into a second mold cavity 33 formed by the material removal device 100 removing a portion of the first solid tooth material 21. In such an embodiment, a fluid-to-solid tooth material curing device such as heater 130 or light 140 may be configured to cure the second fluid synthetic tooth material 30 in the second mold cavity 33 into second solid tooth material 31. Additionally, the material holding fixture (not shown) and material removal device 100 may be movable with respect to each other so as to enable the material removal device 100 to remove second solid tooth material 31 in the second mold cavity 33 so as to form at least a portion of the plurality of teeth 64.

The apparatus may be further comprised of a third fluid synthetic tooth material delivery device (not shown) configured to deliver the third fluid synthetic tooth material into a third mold cavity formed by the material removal device 100 removing a portion of the first and/or second solid tooth materials 21 and 31. In such an embodiment, a fluid-to-solid tooth material curing device such as heater 130 and/or light 140 may be configured to cure the third fluid synthetic tooth material in the third mold cavity into third solid tooth material 41. Additionally, the material holding fixture and material removal device 100 may be movable with respect to each other so as to enable the material removal device 100 to remove third solid tooth material in the third mold cavity so as to form at least a portion of the plurality of teeth 64.

The apparatus may further include a computer for operating the motion of the denture base material holding fixture, the material removal device, the fluid synthetic tooth material delivery device(s), the fluid-to-solid tooth material curing device(s), a heat treating device, and final finishing and polishing devices, to the extent such devices are provided. Accordingly, one or more of the steps of the method may be implemented by the computer. The computer may be located remotely from the remaining components of the apparatus and may be in hardwired or wireless communication with one or more of such components. The computer may include a central processing unit, a memory, a computer-readable storage medium such as a hard disk, optical disk, or flash memory, and a communication interface for wireless or hardwired signal communication with other components of the apparatus and via the Internet or other computer communication network.

The denture to be manufactured may be defined by a digital three-dimensional model. The 3D model may be defined by making measurements and/or scanning of the patient's mouth. Alternatively, as described previously, the 3D model may be made by scanning a "try-in" denture that is fitted by a dentist or other clinician to the patient in order to establish the final dimensions of the denture.

Once the 3D model is completed, it may then be uploaded to and used by the computer to control the denture-making apparatus and perform the steps to produce the final denture as described herein. For example, forming a first cavity, delivering first fluid synthetic tooth material into the first cavity, solidifying the first synthetic fluid tooth material into first solid synthetic tooth material, and removing a portion of the first solid synthetic tooth material to form at least a portion of the plurality of teeth and the removing a portion of the block of denture base material to form the denture base may be performed by the computer to produce the denture having the dimensions defined in the three-dimensional model. The computer may perform the processing of second and third solid synthetic tooth materials in a similar manner, if such are made part of the denture.

It is to be understood that while the present disclosure has been set forth as methods and apparatus for making a denture, the methods and apparatus are not limited to only such an article. The instant method and apparatus are applicable to other dental prostheses such as partial denture prostheses, occlusal splints, nightguards, orthodontic appliances, crowns, bridges, as well as for the fabrication of other medical prostheses comprising first and second materials, wherein the first material can be used to form a mold for receiving liquid second material, curing it into solid second material, and then removing a portion of the first and second material to make the medical prosthesis or a portion thereof.

It is, therefore, apparent that there has been provided, in accordance with the present disclosure, a method and apparatus for the manufacturing of a dental prosthesis, and a denture comprising a base and a plurality of teeth. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

I claim:

1. A method of making a denture comprised of a base and a plurality of teeth joined to the base, the method comprising:
   a) forming a first cavity in a block of a denture base material, the first cavity formed to match the contour of natural teeth as arranged on maxillae or on a mandible;
   b) filling the first cavity with a first fluid synthetic tooth material and solidifying the first fluid synthetic tooth material into a first solid synthetic tooth material;
   c) forming a second cavity by removing a portion of the first solid synthetic tooth material, the second cavity formed to match the contour of natural teeth as arranged for the contour of the first cavity;
   d) filling the second cavity with a second fluid synthetic tooth material and solidifying the second fluid synthetic tooth material into a second solid synthetic tooth material;
   e) removing a portion of the second solid synthetic tooth material to form the plurality of teeth; and
   f) removing a portion of the block of denture base material to form the denture base.

2. The method of claim 1, further comprising heat treating the denture base and plurality of teeth.

3. The method of claim 1, wherein solidifying the first fluid synthetic tooth material is performed by heating the first fluid synthetic tooth material.

4. The method of claim 1, wherein solidifying the first fluid synthetic tooth material is performed by irradiating the first fluid synthetic tooth material.

5. The method of claim 1, wherein solidifying the first fluid synthetic tooth material is performed by self-curing first fluid synthetic tooth material.

6. The method of claim 1, wherein the denture is defined by a digital three-dimensional model, and wherein the forming the first cavity and the forming the second cavity are performed based upon data from the three-dimensional model.

7. The method of claim 6, wherein the removing a portion of the second solid synthetic tooth material to form the plurality of teeth and the removing a portion of the block of denture base material to form the denture base are performed to produce the denture having the dimensions defined in the three-dimensional model.

8. The method of claim 7, further comprising making a trial denture, fitting the trial denture to a patient, scanning the fitted trial denture to obtain scanned denture data, and using the scanned denture data to produce the digital three-dimensional model.

9. The method of claim 1, further comprising filling the second cavity with a third fluid synthetic tooth material, solidifying the third fluid synthetic tooth material into a third solid synthetic tooth material, and removing a portion of the third solid synthetic tooth material to re-form the second cavity, prior to filling the second cavity with the second fluid synthetic tooth material.

10. The method of claim 1, wherein the second solid synthetic tooth material differs from the first solid synthetic tooth material.

11. The method of claim 10, wherein the second solid synthetic tooth material is synthetic translucent tooth enamel material.

12. A method of making a denture comprised of a base and a plurality of teeth joined to the base, the method comprising:
   a) forming a first cavity in a block of a denture base material, the first cavity formed to match the contour of natural teeth as arranged on maxillae or on a mandible;
   b) filling the first cavity with a first fluid synthetic tooth material and solidifying the first fluid synthetic tooth material into a first solid synthetic tooth material;
   c) removing a portion of the first solid synthetic tooth material to form the plurality of teeth; and
   d) removing a portion of the block of denture base material to form the denture base.

13. The method of claim 12, wherein the first solid synthetic tooth material is a wax.

14. The method of claim 12, wherein solidifying the first fluid synthetic tooth material is performed by heating the first fluid synthetic tooth material.

15. The method of claim 12, wherein solidifying the first fluid synthetic tooth material is performed by irradiating the first fluid synthetic tooth material.

16. The method of claim 12, wherein solidifying the first fluid synthetic tooth material is performed by initiating self-curing of the first fluid synthetic tooth material.

17. The method of claim 12, further comprising heat treating the denture base and/or plurality of teeth.

18. The method of claim 12, wherein the denture is defined by a digital three-dimensional model, and wherein the forming the first cavity is performed based upon data from the three-dimensional model.

19. The method of claim 12, wherein the denture is defined by a digital three-dimensional model, and wherein the removing a portion of the first solid synthetic tooth material to form the plurality of teeth and the removing a portion of the block of denture base material to form the denture base are performed to produce the denture having the dimensions defined in the three-dimensional model.

* * * * *